United States Patent [19]

Gerdau et al.

[11] Patent Number: 5,008,423

[45] Date of Patent: Apr. 16, 1991

[54] POLYMERIC HYDRIDOCHLOROSILAZANES AND PROCESSES FOR THEIR PREPARATION

[75] Inventors: Thomas Gerdau, Eppstein/Taunus; Hans-Jerg Kleiner, Kronberg/Taunus; Marcellus Peuckert; Martin Brück, both of Hofheim am Taunus; Fritz Aldinger, Rodenbach, all of Fed. Rep. of Germany

[73] Assignee: Hoechst Aktiengesellschaft, Frankfurt am Main, Fed. Rep. of Germany

[21] Appl. No.: 248,547

[22] Filed: Sep. 22, 1988

[30] Foreign Application Priority Data

Oct. 6, 1987 [DE] Fed. Rep. of Germany ....... 3733727

[51] Int. Cl.$^5$ .......................... C07F 7/10; C08G 77/12
[52] U.S. Cl. ........................................ 556/412; 528/31
[58] Field of Search ............................ 556/912; 528/31

[56] References Cited

U.S. PATENT DOCUMENTS

| | | | |
|---|---|---|---|
| 3,408,379 | 10/1968 | McVannel | 556/412 |
| 4,482,689 | 11/1984 | Haluska | 556/412 X |
| 4,535,007 | 8/1985 | Cannady | 427/226 |
| 4,745,205 | 5/1988 | Halusker | 556/412 |
| 4,806,666 | 2/1989 | Pillot et al. | 556/412 |

FOREIGN PATENT DOCUMENTS

| | | | |
|---|---|---|---|
| 568050 | 6/1987 | Australia | 556/412 |
| 0235486 | 9/1987 | European Pat. Off. | 556/412 |
| 1453660 | 9/1966 | France | 556/412 |

*Primary Examiner*—Paul F. Shaver

[57] ABSTRACT

The invention relates to novel polymeric hydridochlorosilazanes and a process for their preparation. The compounds according to the invention can be converted into polyhydridosilaznes by reaction with ammonia, and these can in turn be pyrolyzed to ceramic material containing silicon nitride. To prepare the polymeric hydridochlorosilazanes, oligohydridoalkylsilazanes $(R^1SiHNH)_n$ are reacted with a dichlorohydridoalkylsilane $R^2SiHCl_2$.

13 Claims, No Drawings

POLYMERIC HYDRIDOCHLOROSILAZANES AND PROCESSES FOR THEIR PREPARATION

DESCRIPTION

The invention relates to novel polymeric hydridochlorosilazanes and a process for their preparation. The polymeric hydridochlorosilazanes according to the invention can be converted into polymeric hydridosilazanes ("polyhydridosilazanes") by reaction with ammonia, and these can in turn be pyrolyzed to ceramic material containing silicon nitride.

The pyrolysis of polysilazanes to give ceramic material containing silicon nitride has already been described in the literature (R.R. Wills et al., Ceramic Bulletin, Volume 62 (1983), 904–915).

Chlorosilanes are as a rule used as starting materials for the preparation of polysilazanes and are reacted with ammonia or primary or secondary amines (U.S. Pat. No. 4,540,803, U.S. Pat. No. 4,543,344, U.S. Pat. No. 4,595,775, U.S. Pat. No. 4,397,828 and U.S. Pat. No. 4,482,669). According to U.S. Pat. No. 4,482,669, a dichlorohydridoalkylsilane of the formula $RSiHCL_2$ is reacted with $NH_3$ to give oligohydridoalkylsilazanes $(RSiHNH)_n$, and these are then condensed, for example with the aid of KH, to give polysilazanes, hydrogen being eliminated.

The present invention provides novel starting materials for polyhydridosilazanes, that is to say polymeric hydridochlorosilazanes.

The present invention relates to a process for the preparation of polymeric hydridochlorosilazanes, which comprises reacting oligohydridoalkylsilazanes of the general formula $(R^1SiHNH)_n$, in which n is about 3 to 12 and $R^1$ denotes an alkyl group having 1 to 6 carbon atoms, with a dichlorohydridoalkylsilane of the general formula $R^2SiHCL_2$, in which $R^2$ denotes an alkyl group having 1 to 6 carbon atoms, at 30° to 300° C. Readily volatile by-products are formed by this process. These by-products are removed during the reaction.

The oligohydridoalkylsilazanes $(R^1SiHNH)^n$, in which n is about 3 to about 12 and which are used as starting substances, can be obtained by reacting a dichlorohydridoalkylsilane of the formula $R^1SiHCL_2$, in which $R^1$ has the above meaning, with excess $NH_3$ in a solvent, as described in U.S. Pat. No. 4,482,669 (see in particular columns 4, 5, 7 and 8 therein). A mixture of linear and cyclic oligomers having various chain lengths n is thereby in general formed.

The radicals $R^1$ and $R^2$ in the oligohydridoalkylsilazanes $(R^1SiHNH)_n$ (also called "oligosilazanes" for short below) and in the dichlorohydridoalkylsilane $R^2SiHCL_2$ (also called "dichloroalkylsilane" for short below) can be identical or different and they preferably have 1 to 3 carbon atoms.

Particularly preferably, $R^1=R^2=CH_3$. The molar ratio of the reactants in the above reaction of dichloroalkylsilane : $R^1SiHNH$ unit of the oligosilazane is preferably about 0.2 : 1 to 1.5 : 1, in particular 0.3 : 1 to 1 : 1.

To react the reactants with one another, the oligosilazanes are preferably introduced first and the dichloroalkylsilane is added. Since the reaction is exothermic, the temperature is preferably kept initially at 30° to 50° C. when the reactants are brought together. The mixture is then heated to temperatures of 100° to 300° C., preferably to 120° to 250° C.

The low-boiling components formed as by-products, such as $RSiHCL_2$, $RSiClH_2$, $RSiCL_3$, HCL, $H_2$ and $NH_3$ (in which $R = R1$ or $R^2$) partly escape during the reaction. When the reaction has ended, the remaining low-boiling constituents are in general removed from the reaction vessel by applying a vacuum.

The majority of the $NH_4CL$ likewise formed in the reaction sublimes out of the reaction mixture in the course of the reaction. Any residue of $NH_4CL$ which remains can be removed from the polymeric hydridochlorosilazane prepared according to the invention by extraction with an inert organic solvent, such as n-hexane, toluene or ether.

The duration of the reaction depends on the rate of heating up and on the reaction temperature. A reaction time of 5 to 7 hours is in general sufficient.

It is also possible to carry out the reaction in an organic solvent. Suitable solvents are those which are inert towards the reactants and have a sufficiently high boiling point, that is to say, for example, saturated aliphatic or aromatic hydrocarbons, such as n-decane, decalin, xylene or toluene, chlorinated hydrocarbons, such as chlorobenzene, or ethers, such as dibenzyl ether or diethylene glycol diethyl ether. If a solvent in which the $NH^4Cl$ formed is insoluble is used, the latter can be separated off by filtration. The polymeric hydridochlorosilazanes according to the invention are then obtained by distilling off the solvent under reduced pressure.

If appropriate, the process can also be carried out under reduced pressure. It can also be carried out under pressures in the range from 1 to 10 atmospheres.

The process can also be carried out continuously.

The novel polymeric hydridochlorosilazanes prepared have a molecular structure which can be represented by the formula

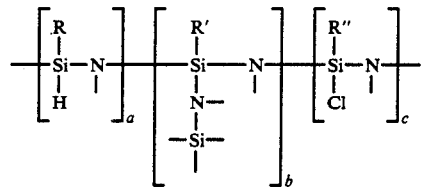

in which the free valencies on the nitrogen atoms are saturated with H atoms or silyl radicals $R^*SiXN<(X=H, CL$ or $N<)$. R, R', R" and R* denote alkyl groups having 1 to 6, preferably 1 to 3, carbon atoms and a, b an c denoted the molar fractions of the particular structural units. $a + b + c = 1$. Particularly preferably, $R = R' = R'' = R^* = CH_3$. The polymeric hydridochlorosilazanes have a network structure.

Accordingly the present invention also relates to polymeric hydridochlorosilazanes of the formula

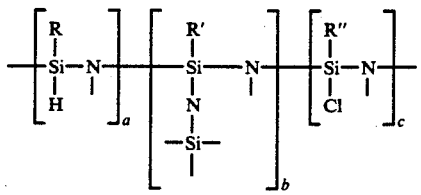

in which the free valencies of the nitrogen atoms are saturated with H atoms or silyl radicals $R^*SiXN<(X$ =H, CL or N<) and in which R, R', R" and R* denote alkyl groups having 1 to 6 carbon atoms and a, b and c denote the molar fractions of the particular structural units.

The values of the molar fractions b and c are higher (and correspondingly the value of a is lower) the greater the ratio of dichloroalkylsilane: $R^1$SiHNH unit of the oligosilazane. The particular values of a, b and c present can be determined by integration of the $^1$H-NMR spectra and by elemental analysis. The values a, b and c are in general 0.1 to 0.8, and a +b +c =1. Those polymeric hydridochlorosilazanes in which the values for a and b are 0.1 to 0.5, in particular 0.2 to 0.4, are preferred. The preferred values of c are 0.1 to 0.6, in particular 0.3 to 0.6. As mentioned, these values can be adjusted via the relative content of the dichloroalkylsilane in the reaction mixture and checked by the analytical methods mentioned. The preferred values just mentioned for a, b and c have proved particularly appropriate if a fiber is to be produced as the end product of the pyrolysis (after conversion of the polymeric hydridochlorosilazanes into polyhydridosilazanes).

The invention furthermore relates to polymeric hydridochlorosilazanes which are prepared by reacting oligohydridoalkylsilazanes of the general formula $(R^1SiHNH)_n$, in which n is about 3 to about 12 and $R^1$ denotes an alkyl group having 1 to 6 carbon atoms, with a dichlorohydridoalkylsilane of the general formula $R^2SiHCL_2$, in which $R^2$ denotes an alkyl group having 1 to 6 carbon atoms, at 30° to 300° C. The readily volatile by-products formed are removed during the reaction.

The novel polymeric hydridochlorosilazanes (also called "polyhydridochlorosilazanes") can be converted into polyhydridosilazanes by reaction with ammonia (ammonolysis"), and these can in turn be converted into ceramic material containing silicon nitride by pyrolysis.

The ammonolysis can be carried out in liquid $NH_3$. However, it is advantageous to carry it out in an organic solvent. Suitable solvents are all those which are inert towards the polyhydridochlorosilazanes. Preferred solvents are those in which the ammonium chloride obtained as a by-product has a low solubility and can easily be separated off, for example ethers, aliphatic and aromatic hydrocarbons and chlorinated hydrocarbons. The reactants can be fed into the reaction vessel in any desired sequence for the ammonolysis. However, it is usually advantageous to initially introduce the polyhydridochlorosilazane initially in solution and to introduce gaseous ammonia or to add liquid ammonia. If the polyhydridochlorosilazanes according to the invention have been prepared in a suitable organic solvent, the ammonolysis can be carried out in this solvent without prior removal of the $NH_4CL$. The ammonolysis is preferably carried out with an excess of $NH_3$, in order to ensure that the reaction is complete and the end products are substantially free from chlorine as far as possible. Twice the stoichiometric amount is in general sufficient for this purpose.

The reaction is in general carried out at a temperature of about −50° to +100° C., preferably at −20° to +30° C. and in particular at room temperature (the mixture being cooled with ice). However, it is also possible to carry out the reaction above room temperature, for example at the boiling point of the solvent used, or below room temperature, for example at −33° C., if liquid $NH_3$ is used.

When the ammonolysis has ended, the excess $NH_3$ is removed, if appropriate, and the ammonium chloride obtained is filtered off. To increase the yield, the precipitate can be washed with one of the abovementioned organic solvents. After the solvent has been distilled off under reduced pressure, the polyhydridosilazanes according to the invention are obtained directly as white powders. The polyhydridosilazanes are soluble in the above organic solvents, so that these can be used both for coating surfaces and for the production of fibers.

The polyhydridosilazanes can be pyrolyzed by pyrolysis in an inert nitrogen or argon atmosphere at temperatures of 800° to 1200° C. to give amorphous dense materials which essentially consist of Si, N and C and can also contain traces of H and 0. At pyrolysis temperatures above 1200° C., for example in the range from 1200° C. to 1400° C., partly amorphous microcrystalline ceramic materials containing $\alpha$-$Si_3N_4$ as the crystalline phase are formed.

It is a particular advantage that the polyhydridosilazanes can be shaped by various processes before the pyrolysis to give three-dimensional shaped articles.

An important method of shaping is drawing of fibers. Specifically fibers can be drawn from highly viscous solutions of the polyhydridosilazane in solvents such as toluene, tetrahydrofuran or hexane. The fibers are advantageously drawn by means of spinnerets 80 to 150 $\mu$m in diameter. The threads are narrowed by subsequent stretching, so that a very solid thread of 2 to 20 $\mu$m, in particular 5 to 15 $\mu$m, in diameter is formed after the pyrolysis. The fibers produced by subsequent pyrolysis are used as mechanical reinforcing inclusions in fiber-reinforced aluminum, aluminum alloys and ceramic components.

Another important processing possibility for the polyhydridosilazanes is the production of dense, firmly adhering, amorphous or microcrystalline ceramic coatings on metals, in particular steels, or on ceramics, such as $AL_2O_3$, $ZrO_2$, MgO, SiC or $Si_3N_4$. Coating is effected with the aid of a solution of the polyhydridosilazane in organic solvents, such as toluene, tetrahydrofuran and hexane. The pyrolytic conversion into an amorphous or microcrystalline layer is carried out in the same temperature range of 800° to 1200° C. or 1200° to 1400° C. under an inert gas as described above for three-dimensional shaped articles.

Because of their outstanding adhesion, good hardness and surface quality, the ceramic coatings are particularly suitable for surface-finishing of machine components subjected to mechanical and chemical stresses.

The polyhydridosilazanes described above can furthermore also be pyrolyzed in an $NH_3$ atmosphere, instead of in an inert gas, with an equivalent ceramic yield of 70 to 90%. The result is a practically carbon-free, glass-clear colorless material. On pyrolysis in $NH_3$ at 1000° C. or more, the C content is less than 0.5% by weight. Depending on the pyrolysis temperature, the pyrolysis product consists of practically pure amorphous silicon nitride (pyrolysis below 1200° C.) or crystalline $Si_3N_4$ (pyrolysis above 1200° C., in particular above 1300° C.). The pyrolysis in $NH_3$ can be used on all the shaped articles produced by the shaping processes described above, that is to say articles, fibers and coatings shaped from powders.

EXPERIMENTAL REPORT

Preparation of oligohydridomethylsilazane (CH₃SiHNH)ₙ

100 ml (0.97 mol) of methyldichlorosilane were dissolved in 800 ml of absolute tetrahydrofuran and ammonia was passed in for 3 hours (rate of introduction: 0.5 l/minute). The reaction temperature was kept in the range from 20° to 25° C. by cooling with an ice-bath. The mixture was stirred at room temperature for 1 hour in order to bring the reaction to completion and the ammonium chloride was then removed under argon. The precipitate was washed twice with 350 ml of tetrahydrofuran each time and the combined tetrahydrofuran solutions were concentrated under reduced pressure. A clear, highly mobile oil of (CH₃SiHNH)ₙ was obtained in a yield of 44.5 g =78% of theory.

EXAMPLES

Preparation of polymeric hydridochlorosilazane

Example 1

176.1 g (1.53 mol) of methyldichlorosilane were added to 108.8 g (1.84 mol) of oligohydridomethylsilazane at 30° to 45° C. and the mixture was heated to 200° C. in an oilbath in the course of 7 hours. During this the internal temperature rose from 46° C. to 164° C. Above 100° C., vigorous evolution of gas started. When the reaction had ended and the mixture had cooled, a brittle resin was obtained. The total contents of the reaction flask were 134 g. The resin was extracted with 500 ml of tetrahydrofuran, the residue was then washed with 50 ml of n-hexane and the organic solvent was stripped off in vacuo. 109 g of a white powder having the chemical composition $C_1H_{3.62}CL_{0.38}N_{0.8}Si_1$ remained.

Elemental analysis (% by weight): Found: 19.1% of Cl; 39.8% of Si; 16.2% of N; 16.5% of C; 6.8% of H Calculated: 19.7% of Cl; 41.0% of Si; 16.4% of N; 17.6% of C; 5.3% of H Molar mass: 1,865 g/mol, determined by osmometry in benzene $^1$H—NMR (100 MHz,CDCL₃,ppm): δ0.2–0.8 (br,3H,SiCH₃), 1.5–1.9 (br,0.1H,NH), 4.5 (br), 4.7–5.0 (br) and 5.1 (br,0.4H,SiH).

IR: (KBr,cm$^{-1}$) 3380 (sh), 3150 (br,vs), 3050 (s), 2840 (w), 2160 (s), 1410 (vs), 1270 (vs), 1200–950 (br), 900 (br,vs), 760 (br,s).

Example 2

1.55 g (135 mmol) of methyldichlorosilane were added to 11.3 g (190 mmol) of oligohydridomethylsilazane. During this the internal temperature thereby rose to 50° C. The reaction mixture was heated to an internal temperature of 160° C. in the course of 30 minutes and kept at this temperature for 1.5 hours. Heating was then continued at an internal temperature of 180° to 190° C. for 4 hours. After the low-boiling reaction products had been stripped off, the cooled residue was extracted with 150 ml of n-pentane, and, after evaporation 10.1 g of a white soluble powder consisting of polyhydridochlorosilazane were obtained.

Elemental analysis (% by weight):
41% of Si 17.6% of N 15.3% of Cl

Example 3

10.9 g (184 mmol) of oligohydridomethylsilazane and 17.6 g (153 mmol) of methyldichlorosilane were boiled under reflux in an oilbath at a bath temperature of 225° to 235° C. for 7 hours. Low-boiling constituents were stripped off at an internal temperature of 80° C. by applying a vacuum. The residue was dissolved in 50 ml of tetrahydrofuran and the solution was filtered. After the solvent had been stripped off, 10.0 g of a white soluble powder consisting of polyhydridochlorosilazane remained.

Elemental analysis (% by weight):
34% of Si 15.9% of N 22% of Cl

We claim:

1. A process for the preparation of a polymeric hydridochlorosilazane, which comprises reacting an oligohydridoalkylsilazane of the formula (R$^1$SiHNH)ₙ, in which n is 3 to 12 and R$^1$ denotes an alkyl group with 1 to 6 carbon atoms, with a dichlorohydridoalkylsilane of the formula R$^2$SiHCL₂, in which R$^2$ denotes an alkyl group having 1 to 6 carbon atoms, at 30° to 300° C.

2. A process for the preparation of a polymeric hydridochlorosilazane, which comprises reacting an oligohydridoalkylsilazane which has been obtained by reacting a dichlorohydridoalkylsilane R$^1$SiHCL₂ with NH₃ with a dichlorohydridoalkylsilane of the formula R$^2$SiHCL₂ at 30° to 300° C., R$^1$ and R$^2$ denoting alkyl groups having 1 to 6 carbon atoms.

3. The process as claimed in claim 1, wherein R$^1$ and R$^2$ denote alkyl groups having 1 to 3 carbon atoms.

4. The process as claimed in claim 1, wherein R$^1$=R$^2$=CH₃.

5. The process as claimed in claim 1, wherein the molar ratio of dichlorohydridoalkylsilane R$^2$SiHCL₂ to an R$^1$SiHNH unit of the oligohydridoalkylsilazane is 0.2 : 1 to 1.5 : 1.

6. The process as claimed in claim 1, wherein a temperature of 30° to 50° C. is maintained when the reactants are brought together and the mixture is then heated to 100° to 300° C.

7. A polymeric hydridochlorosilazane of the formula

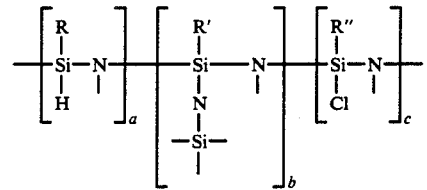

in which the free valencies of the nitrogen atoms are saturated with H atoms or silyl radicals R*SiX-N<(X=H,Cl or N<) and in which R, R', R" and R* denote alkyl groups having 1 to 6 carbon atoms and a, b and c have values ranging from 0.1 to 0.8 and denote the molar fractions of the particular structural units.

8. A polymeric hydridochlorosilazane as claimed in claim 7, wherein R, R', R" and R* are alkyl groups having 1 to 3 carbon atoms.

9. A polymeric hydridochlorosilazane as claimed in claim 7, wherein R =R'=R"=R* =CH₃.

10. A polymeric hydridochlorosilazane obtainable by the process as claimed in claim 1.

11. A polymeric hydridochlorosilazane obtainable by the process as claimed in claim 2.

12. A polymeric hydridochlorosilazane obtainable by the process as claimed in claim 3.

13. A polymeric hydridochlorosilazane obtainable by the process as claimed in claim 4.

* * * * *